Dec. 29, 1959 H. KLEINE Plant Pat. 1,891
VIBURNUM TOMENTOSUM PLANTS
Filed Oct. 28, 1958
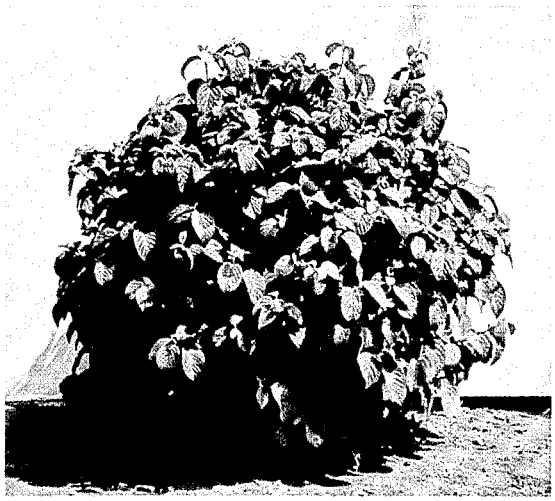
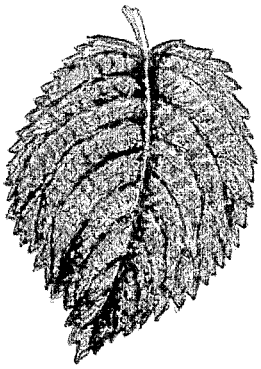
INVENTOR
Henry Kleine
By Orville M. Kile
Plant Patent Agt.

United States Patent Office

Plant Pat. 1,891
Patented Dec. 29, 1959

1,891

VIBURNUM TOMENTOSUM PLANTS

Henry Kleine, Newport, Mich.

Application October 28, 1958, Serial No. 770,246

1 Claim. (Cl. 47—59)

Outstanding among the characteristics of this new variety are its dwarf, compact, globe-like growth and the relatively small size of its leaves which are about half as long and half as wide as typical leaf of the species.

This new variety originated at my nurseries in Newport, Michigan. It resulted as a selected seeding among many grown by me and its parents are varieties of *Viburnum tomentosum* Thunb. Many thousands of seedlings are grown at my nurseries from which are selected the best specimens, these being carefully watched for outstanding qualities. Of the approximately 100 seedlings which were planted in a row seven years ago, the original plant of this new variety is the only one with this typical dwarf and globose growing habit. All the others have now reached a height of 5 to 6 feet.

I have asexually reproduced this new variety at my nurseries in Michigan, by means of layering, and its distinguishing qualities appear to be permanent.

The accompanying illustrations show a bush of my new variety in approximately its natural colors, showing particularly the dwarf, globular form of the bush, also a typical leaf in true colors and natural size as grown in the State of Michigan in the month of August.

Following is a more detailed description of my new variety, in which referenec to color indicates the ordinary dictionary meaning of color terms, except as otherwise noted, inasmuch as color is not involved in the claims.

Growth habit: Slow-growing, dwarf shrub.

Shape: Compact; globular.

Health: Hardy as far north as New England. Apparently free from insect pests and not readily subject to disease. Has withstood temperatures of 10° below zero.

Leaves:

*Color.*—Approximately Moderate Yellow Green, 5GY 5/6 (Nickerson Color Fan).

*Surface.*—Ridged. Veins prominent and brownish-red in color. There is also a slight edging of similar color around each leaf.

*Shape.*—Broadly ovate, with rounded base and acute apex. Not quite symmetrical. Edge dentate-serrate.

*Leaf-stem.*—Short and reddish colored as it approaches maturity.

*Size.*—Small, averaging 2⅛ inches long and 1½ inches wide. The leaves will vary somewhat in size depending on the environment and whether taken from the tip or the base of a branch, but they are all definitely smaller than those of the usual *tomentosum* variety grown under similar conditions.

Flower: This variety has produced no flowers, partly because the original plan (as well as its asexual reproductions) is relatively young, but also because cutting wood has been taken for propagation purposes. However, the flower will be of the flat-cyme type since the variety originated as a seedling and could have come from this type only, because the globose-flowering type is incapable of producing seed.

Having thus disclosed my discovery, I claim:

The new and distinct variety of *Virbunum tomentosum* Thunb. plant, substantially as herein shown and described, characterized particularly as to novelty by its very dwarf, compact, and almost globe-shaped growth; and the comparatively small size of its leaves.

No references cited.